(12) United States Patent
Moore et al.

(10) Patent No.: US 11,285,016 B2
(45) Date of Patent: Mar. 29, 2022

(54) VERTEBRAL PLATE SYSTEMS AND METHODS OF USE

(71) Applicant: K2M, Inc., Leesburg, VA (US)

(72) Inventors: Jennifer Moore, Leesburg, VA (US); Clint Boyd, Winchester, VA (US); Megan Carnes, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 130 days.

(21) Appl. No.: 16/599,736

(22) Filed: Oct. 11, 2019

(65) Prior Publication Data

US 2020/0121470 A1 Apr. 23, 2020

Related U.S. Application Data

(63) Continuation of application No. 15/007,348, filed on Jan. 27, 2016, now abandoned.
(Continued)

(51) Int. Cl.
*A61F 2/44* (2006.01)
*A61B 17/86* (2006.01)
(Continued)

(52) U.S. Cl.
CPC ........ *A61F 2/4455* (2013.01); *A61B 17/7059* (2013.01); *A61B 17/8625* (2013.01); *A61F 2/44* (2013.01); *A61F 2/447* (2013.01); *A61F 2/4465* (2013.01); *A61F 2002/3092* (2013.01); *A61F 2002/3093* (2013.01); *A61F 2002/30593* (2013.01); *A61F 2002/30622* (2013.01);
(Continued)

(58) Field of Classification Search
CPC ........ A61F 2/4455; A61F 2/44; A61F 2/4465; A61F 2/447; A61F 2002/30593; A61F 2002/30622; A61F 2002/30784; A61F 2002/30904; A61F 2002/3092; A61F 2002/3093
USPC .................................. 606/70–71, 280–299
See application file for complete search history.

(56) References Cited

U.S. PATENT DOCUMENTS 5,192,327 A 3/1993 Brantigan
5,201,737 A * 4/1993 Leibinger ............ A61B 17/688
606/280
(Continued)

FOREIGN PATENT DOCUMENTS

CN 103445883 A 12/2013
DE 102008024281 A1 12/2009
(Continued)

OTHER PUBLICATIONS

International Search Report and Written Opinion for PCT/US16/56834 dated Jan. 12, 2017.
(Continued)

*Primary Examiner* — Jessica Weiss
(74) *Attorney, Agent, or Firm* — Lerner, David, Littenberg, Krumholz & Mentlik, LLP

(57) ABSTRACT

A vertebral plate includes a top and bottom surface, a plurality of orifices defined through at least one of the top and bottom surfaces, and a plurality of bone screw openings defined through the top and bottom surfaces. The plurality of orifices defined through the top surface includes a different cross-section than a plurality of orifices defined through the bottom surface. A vertebral plate system and a method of use are also provided.

20 Claims, 5 Drawing Sheets

Related U.S. Application Data

(60) Provisional application No. 62/196,371, filed on Jul. 24, 2015, provisional application No. 62/108,197, filed on Jan. 27, 2015.

(51) Int. Cl.
   *A61B 17/70* (2006.01)
   *A61F 2/30* (2006.01)

(52) U.S. Cl.
   CPC .............. *A61F 2002/30784* (2013.01); *A61F 2002/30904* (2013.01); *A61F 2310/00023* (2013.01)

(56) References Cited

U.S. PATENT DOCUMENTS

| | | |
|---|---|---|
| 5,534,031 A | 7/1996 | Matsuzaki et al. |
| 5,595,703 A | 1/1997 | Swaelens et al. |
| 5,609,635 A | 3/1997 | Michelson |
| 5,634,926 A | 6/1997 | Jobe |
| 5,702,449 A | 12/1997 | McKay |
| 5,733,286 A | 3/1998 | Errico et al. |
| 5,768,134 A | 6/1998 | Swaelens et al. |
| 5,786,134 A | 7/1998 | Nair et al. |
| 5,943,235 A | 8/1999 | Earl et al. |
| 5,968,098 A | 10/1999 | Winslow |
| 6,010,502 A | 1/2000 | Bagby |
| 6,039,762 A | 3/2000 | McKay |
| 6,129,730 A | 10/2000 | Bono et al. |
| 6,342,055 B1 | 1/2002 | Eisermann et al. |
| 6,391,058 B1 | 5/2002 | Kuslich et al. |
| 6,432,107 B1 | 8/2002 | Ferree |
| 6,454,811 B1 | 9/2002 | Sherwood et al. |
| 6,520,996 B1 | 2/2003 | Manasas et al. |
| 6,530,955 B2 | 3/2003 | Boyle et al. |
| 6,530,956 B1 | 3/2003 | Mansmann |
| 6,716,247 B2 | 4/2004 | Michelson |
| 6,730,127 B2 | 5/2004 | Michelson |
| 6,758,849 B1 | 7/2004 | Michelson |
| 6,855,167 B2 | 2/2005 | Shimp et al. |
| 7,238,206 B2 | 7/2007 | Lange et al. |
| 7,509,183 B2 | 3/2009 | Lin et al. |
| 7,645,301 B2 | 1/2010 | Hudgins et al. |
| 7,665,979 B2 | 2/2010 | Heugel |
| 7,806,911 B2 | 10/2010 | Peckham |
| 7,909,872 B2 | 3/2011 | Zipnick et al. |
| D664,252 S | 7/2012 | Weiland et al. |
| 8,275,594 B2 | 9/2012 | Lin et al. |
| 8,403,986 B2 | 3/2013 | Michelson |
| 8,439,977 B2 | 5/2013 | Kostuik et al. |
| 8,449,585 B2 | 5/2013 | Wallenstein et al. |
| 8,585,761 B2 | 11/2013 | Theofilos |
| 8,590,157 B2 | 11/2013 | Kruth et al. |
| 8,673,011 B2 | 3/2014 | Theofilos et al. |
| 8,697,231 B2 | 4/2014 | Longepied et al. |
| 8,784,721 B2 | 7/2014 | Philippi et al. |
| 8,801,791 B2 | 8/2014 | Soo et al. |
| 8,814,919 B2 | 8/2014 | Barrus et al. |
| 8,843,229 B2 | 9/2014 | Vanasse et al. |
| 8,870,957 B2 | 10/2014 | Vraney et al. |
| 8,903,533 B2 | 12/2014 | Eggers et al. |
| 8,932,356 B2 | 1/2015 | Kraus |
| 8,961,517 B2 | 2/2015 | McClintock et al. |
| 8,967,990 B2 | 3/2015 | Weidinger et al. |
| 8,999,711 B2 | 4/2015 | Harlow et al. |
| 9,011,982 B2 | 4/2015 | Muller et al. |
| 9,283,078 B2 | 3/2016 | Roels et al. |
| D786,434 S | 5/2017 | Trautwein |
| 9,700,431 B2 | 7/2017 | Nebosky et al. |
| 9,931,148 B2 | 4/2018 | Grady, Jr. et al. |
| 10,028,841 B2 | 7/2018 | Moore et al. |
| 2001/0047207 A1 | 11/2001 | Michelson |
| 2001/0047208 A1 | 11/2001 | Michelson |
| 2002/0128714 A1 | 9/2002 | Manasas et al. |
| 2003/0040798 A1 | 2/2003 | Michelson |
| 2003/0135276 A1 | 7/2003 | Eckman |
| 2004/0024400 A1 | 2/2004 | Michelson |
| 2004/0034352 A1 | 2/2004 | Needham et al. |
| 2004/0243237 A1 | 12/2004 | Unwin et al. |
| 2004/0249471 A1 | 12/2004 | Bindseil et al. |
| 2005/0010226 A1 | 1/2005 | Grady et al. |
| 2005/0021151 A1 | 1/2005 | Landis |
| 2005/0055099 A1 | 3/2005 | Ku |
| 2005/0112397 A1 | 5/2005 | Rolfe et al. |
| 2005/0137597 A1 | 6/2005 | Butler et al. |
| 2005/0149192 A1 | 7/2005 | Zucherman et al. |
| 2005/0165400 A1 | 7/2005 | Fernandez |
| 2005/0177238 A1 | 8/2005 | Khandkar et al. |
| 2005/0246021 A1 | 11/2005 | Ringeisen et al. |
| 2006/0235403 A1 | 10/2006 | Blain |
| 2006/0264946 A1 | 11/2006 | Young |
| 2007/0055249 A1 * | 3/2007 | Jensen ............... A61B 17/8863 606/288 |
| 2007/0233272 A1 | 10/2007 | Boyce et al. |
| 2007/0260324 A1 | 11/2007 | Joshi et al. |
| 2007/0270812 A1 * | 11/2007 | Peckham ............ A61B 17/7068 606/279 |
| 2007/0270965 A1 | 11/2007 | Ferguson |
| 2008/0009872 A1 * | 1/2008 | Vaughen ............ A61B 17/8085 606/71 |
| 2008/0097444 A1 | 4/2008 | Erickson et al. |
| 2008/0312743 A1 | 12/2008 | Vila et al. |
| 2009/0018584 A1 | 1/2009 | Henderson, Sr. et al. |
| 2009/0030467 A1 * | 1/2009 | Sonohata ............ A61B 17/808 606/280 |
| 2009/0048675 A1 * | 2/2009 | Bhatnagar .......... A61B 17/7233 623/17.16 |
| 2009/0054930 A1 | 2/2009 | Aflatoon |
| 2009/0093881 A1 | 4/2009 | Bandyopadhyay et al. |
| 2009/0270986 A1 | 10/2009 | Christensen |
| 2009/0291308 A1 | 11/2009 | Pfister et al. |
| 2009/0295042 A1 | 12/2009 | Pfister et al. |
| 2010/0004747 A1 | 1/2010 | Lin |
| 2010/0100131 A1 | 4/2010 | Wallenstein |
| 2010/0137990 A1 | 6/2010 | Apatsidis et al. |
| 2010/0228369 A1 | 9/2010 | Eggers et al. |
| 2010/0234966 A1 | 9/2010 | Lo |
| 2010/0268339 A1 | 10/2010 | Malinin et al. |
| 2011/0054542 A1 * | 3/2011 | Kevin ................ A61B 17/7059 606/289 |
| 2011/0144752 A1 | 6/2011 | Defelice et al. |
| 2011/0165340 A1 | 7/2011 | Baumann |
| 2011/0168091 A1 | 7/2011 | Baumann et al. |
| 2011/0190888 A1 | 8/2011 | Bertele et al. |
| 2011/0190904 A1 | 8/2011 | Lechmann et al. |
| 2011/0301709 A1 | 12/2011 | Kraus et al. |
| 2012/0046750 A1 | 2/2012 | Obrigkeit et al. |
| 2012/0143334 A1 | 6/2012 | Boyce et al. |
| 2012/0158062 A1 | 6/2012 | Nunley et al. |
| 2012/0179261 A1 | 7/2012 | Soo |
| 2012/0191188 A1 | 7/2012 | Huang |
| 2012/0191189 A1 | 7/2012 | Huang |
| 2012/0203229 A1 | 8/2012 | Appenzeller et al. |
| 2012/0303128 A1 | 11/2012 | Ullrich, Jr. et al. |
| 2012/0310364 A1 | 12/2012 | Li et al. |
| 2012/0316650 A1 | 12/2012 | Ullrich, Jr. et al. |
| 2013/0046345 A1 | 2/2013 | Jones et al. |
| 2013/0110243 A1 | 5/2013 | Patterson et al. |
| 2013/0116793 A1 | 5/2013 | Kloss |
| 2013/0150893 A1 | 6/2013 | Kirschman |
| 2013/0171019 A1 | 7/2013 | Gessler et al. |
| 2013/0184765 A1 | 7/2013 | Beyar et al. |
| 2013/0273131 A1 | 10/2013 | Frangov et al. |
| 2014/0088716 A1 | 3/2014 | Zubok et al. |
| 2014/0107785 A1 | 4/2014 | Geisler et al. |
| 2014/0107786 A1 | 4/2014 | Geisler et al. |
| 2014/0172111 A1 | 6/2014 | Lang et al. |
| 2014/0243901 A1 * | 8/2014 | Mebarak ............ A61B 17/809 606/281 |
| 2014/0277491 A1 | 9/2014 | Fang et al. |
| 2014/0309699 A1 * | 10/2014 | Houff ................ A61B 17/842 606/281 |
| 2015/0018956 A1 | 1/2015 | Steinmann et al. |

(56) References Cited

U.S. PATENT DOCUMENTS

| | | |
|---|---|---|
| 2015/0025573 A1 | 1/2015 | Abitbol et al. |
| 2015/0045924 A1 | 2/2015 | Cluckers et al. |
| 2015/0134063 A1 | 5/2015 | Steinmann et al. |
| 2015/0142062 A1 | 5/2015 | Donald et al. |
| 2015/0142158 A1 | 5/2015 | Szwedka |
| 2015/0367575 A1 | 12/2015 | Roels et al. |
| 2016/0022431 A1 | 1/2016 | Wickham |
| 2016/0038301 A1 | 2/2016 | Wickham |
| 2016/0058575 A1 | 3/2016 | Sutterlin, III et al. |
| 2016/0183990 A1* | 6/2016 | Koizumi ............... B23K 26/38 606/285 |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2019/0298542 A1 | 10/2019 | Kloss |
| 2019/0328546 A1 | 10/2019 | Palagi et al. |

FOREIGN PATENT DOCUMENTS

| | | |
|---|---|---|
| DE | 102008024288 A1 | 12/2009 |
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011030017 A1 | 3/2011 |
| WO | 201317647 A1 | 2/2013 |
| WO | 2013155500 A1 | 10/2013 |
| WO | 2013156545 A1 | 10/2013 |
| WO | 201496294 A1 | 6/2014 |

OTHER PUBLICATIONS

Akamaru et al., Healing of Autologous Bone in a Titanium Mesh Cage Used in Anterior Column Reconstruction After Total Spondylectomy; SPINE vol. 27, No. 13, pp. E329-E333, Jan. 2002.

Bridwell et al.., Specialty Update, What's New in Spine Surgery, The Journal of Bone and Joint Surgery, Incorporated, pp. 1022-1030, Core 1st page of article, 2015.

Cheung et al., Spinal Instrumentation Overview in Lumbar Degenerative Disorders: Cages, Lumbar Spine: Official Publication of the International Society for the Study of Lumbar Spine (3), pp. 286-291, 2004.

Chong et al., The design evolution of interbody cages in anterior cervical discectomy and fusion: a systematic review; BMC Musculoskeletal Disorders 2015 16:99, pp. 1-20.

Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.

Cunnigham et al, Design of Interbody Fusion Cages: Historical Considerations and Current Perspectives in Cage Technology; Surgical Techniques, Spinal Implants, pp. 421-465, 2006.

EBI Spine Flyer, North American Spine Society 20th Annual Meeting, Sep. 27-Oct. 1, 2005.

Extended European Search Report for EP 16 15 2952 dated Jul. 1, 2016.

Extended European Search Report including the Written Opinion for Application No. EP 16856190.0 dated May 28, 2019.

Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 1, 2011;1, 3 pages.

Kim et al. Spinal Instrumentation Surgical Techniques, Thieme Medical publishers, 2004, pp. 232-245, 518-524, p. 32-537, 736-743, 795-800.

Kuslich, Lumbar Interbody Cage Fusion for Back Pain: An Update on the Bak (Bagby and Kuslich) System, SPINE: State of the Art Reviews; vol. 13, No. 2, May 1999, pp. 295-311.

Lin et al., Interbody Fusion Gage Design Using Integrated Global Layout and Local Microstructure Topology Optimization; SPINE, vol. 29, No. 16, pp. 1747-1754,2004.

Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.

McAfee, Interbody Fusion Cages in Reconstructive Operations on the Spine, The Journal of Bone and Joint Surgery Incorporated, vol. 81A, No. 6, Jun. 1999, pp. 859-880.

Sasso, Screws, Cages or Both?, <http://www.spineuniverse.com/professional/technology/surgical/thoracic/>, pp. 1-11, Sep. 2012.

Sofamor Danek Interfix Thread Fusion Device, pp. 32-45, 1999.

Stryker, Ttritanium basic science summary, technical monograph, pp. 1-2, 2016.

Synthes Contact Fusion Cage, Technique Guide, 2007, pp. 1-16.

Williams et al., CT Evaluation of Lumbar Interbody Fusion: Current Concepts, AJNR Am J Neuroradiol 26:2057-2066, Sep. 2005.

Zdeblick, et al., L T-CAGE Lumbar Tapered Fusion Device Surgical Technique, Medtronic, pp. 1-25, 2000.

Australian Examination Report for Application No. 2016200443 dated Sep. 11, 2019, 4 pages.

\* cited by examiner

VERTEBRAL PLATE SYSTEMS AND METHODS OF USE

CROSS-REFERENCE TO RELATED APPLICATIONS

The present application is a continuation of U.S. patent application Ser. No. 15/007,348, filed Jan. 27, 2016, which claims priority to, and the benefit of, U.S. Provisional Patent Application Ser. No. 62/108,197, filed on Jan. 27, 2015 and U.S. Provisional Patent Application Ser. No. 62/196,371, filed on Jul. 24, 2015, the entireties of which are hereby incorporated by reference herein.

BACKGROUND

Technical Field

The present disclosure relates generally to devices and methods for treating spinal conditions, and in particular, to vertebral plate systems and methods for fixation and stabilization of the spine.

Background of the Disclosure

The human spinal column is a highly complex structure. It includes more than twenty discrete bones, known as vertebrae, coupled sequentially to one another to house and protect critical elements of the nervous system. The cervical portion of the spine, which comprises the top of the spine up to the base of the skull, includes the first seven vertebrae.

For many reasons, such as aging and trauma, the intervertebral discs may begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. However, should the prosthetic protrude from between the adjacent vertebrae and thereby contact the surrounding nerves or tissues, the patient may experience additional discomfort. In procedures for remedying this problem, a vertebral plate system having one or more apertures and one or more bone screws is affixed to the vertebrae and oriented to prevent such protrusion.

A common problem associated with the use of such a vertebral plate system is the tendency of the bone screws to "back out" or pull away or otherwise withdraw from the bone into which they are mounted. This problem occurs, primarily, due to the normal torsional and bending motions of the body and spine. As the screws become loose and pull away or withdraw from the bone, the heads of the screws can rise above the surface of the vertebral plate, which results is pain and discomfort for the patient or possibly the separation of the vertebral plate from one or more vertebrae.

Therefore, a need exists for a vertebral plate that inhibits separation of the vertebral plate from a vertebral body.

SUMMARY

In accordance with an embodiment of the present disclosure, there is provided a vertebral plate including a top and bottom surface, a plurality of orifices defined through at least one of the top and bottom surfaces, and a plurality of bone screw openings defined through the top and bottom surfaces. The plurality of orifices defined through the top surface including a different cross-section than a plurality of orifices defined through the bottom surface.

In embodiments, the vertebral plate may include a lip defined within each bone screw opening of the plurality of bone screw openings, wherein the lip is configured to engage a corresponding bone screw to retain the corresponding bone screw therein.

In embodiments, the top and bottom surfaces may include concave curvatures. The concave curvatures of the top and bottom surfaces may extend in the cephalad/caudal direction. Alternatively, the concave curvatures of the top and bottom surfaces may extend in a medial/lateral direction. Further still, the concave curvatures of the top and bottom surfaces may extend in both a cephalad/caudal direction and a medial/lateral direction.

In embodiments, the vertebral plate may be formed using an additive manufacturing process. The vertebral plate may be formed using Selective Laser Powder Processing.

In embodiments, the plurality of orifices defined through the top surface may be offset from the plurality of orifices defined through the bottom surface.

In accordance with an embodiment of the present disclosure, a vertebral plate system is provided, including a vertebral plate and a plurality of bone screws. The vertebral plate includes a top and bottom surface, a plurality of orifices defined through at least one of the top and bottom surfaces, and a plurality of bone screw openings defined through the top and bottom surfaces. The plurality of orifices defined through the top surface includes a different cross-section than the plurality of orifices defined through the bottom surface. The plurality of bone screws are configured to be advanced within the plurality of bone screw openings and driven into a bone.

In embodiments, the plurality of bone screws may be semi-constrained bone screws. The plurality of semi-constrained bone screws may include a shank having a first helical thread disposed thereon and a second helical thread disposed on a head portion thereof. The pitch of the first helical thread may be different than the pitch of the second helical thread, such that the first helical thread threads into vertebral bone whereas the second helical thread engages a lip disposed within each one of the plurality of bone screw openings, thereby retaining the semi-constrained bone screw within the vertebral plate.

In embodiments, the plurality of orifices defined through the top surface may be offset from a plurality of orifices defined through the bottom surface.

In accordance with another embodiment of the present disclosure, a method of performing spinal surgery is disclosed. The method includes inserting a vertebral plate into an incision of a patient, the vertebral plate including a top and a bottom surface, a plurality of orifices defined through at least one of the top and bottom surfaces, and a plurality of bone screw openings defined through the top and bottom surfaces. The plurality of orifices defined through the top surface includes a different cross-section than a plurality of orifices defined through the bottom surface. The method further includes advancing a plurality of bone screws within each bone screw opening of the plurality of bone screw openings and driving each bone screw of the plurality of bone screws into a bone.

In embodiments, the method may include applying a material to the vertebral plate to promote bone ingrowth within the plurality of orifices.

In embodiments, driving each bone screw of the plurality of bone screws into a bone may include driving a plurality of semi-constrained bone screws into a bone.

In embodiments, driving each bone screw of the plurality of bone screws into a vertebra may include threading a first helical thread disposed on a shank of the semi-constrained bone screw into a vertebra and engaging a second helical thread disposed on a head of the semi-constrained bone screw with a lip disposed within each bone screw opening of the plurality of bone screw openings, thereby retaining the plurality of semi-constrained bone screws within the vertebral plate.

In embodiments, the method may include advancing an interbody spacer within a prepared intervertebral space.

In embodiments, applying a material to the vertebral plate may include applying a bone growth putty to the vertebral plate to promote bone ingrowth within the plurality of orifices.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Figure 1:
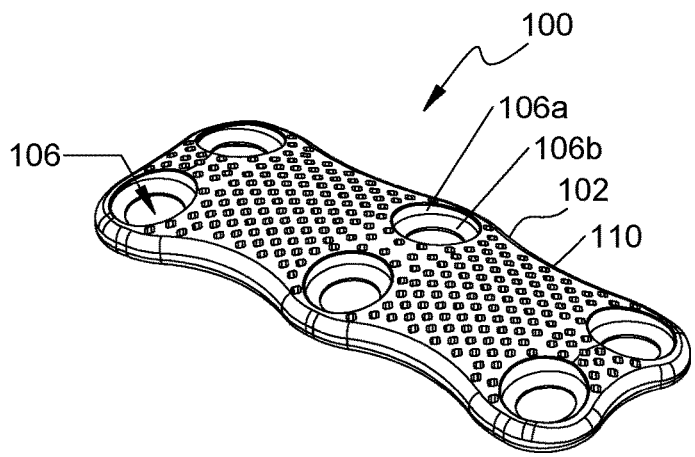
FIG. 1 is a perspective view of a vertebral plate provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudal" indicates a direction toward the patient's feet. Further still, for the purposes of this application, the term "lateral" indicates a direction toward a side of the body of the patient, i.e., away from the middle of the body of the patient, and the term "medial" indicates a direction toward the inside of the body of the patient, i.e., toward the middle of the body of the patient. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to the drawings, FIG. 1 illustrates an embodiment of a vertebral plate 100 provided in accordance with the present disclosure. Vertebral plate 100 includes a top surface 102 and a bottom surface 104 defining a thickness of vertebral plate 100. Vertebral plate 100 may be substantially planar or contoured in either or both the cephalad/caudal and/or medial/lateral planes. As can be appreciated, top surface 102 and bottom surface 104 may include concave contours having the same or different radius of curvature, depending on the application or needs of the patient. In one non-limiting embodiment, top surface 102 and bottom surface 104 of vertebral plate are configured to include concave contours having the same radius of curvature.

Although generally illustrated as including a rectangular profile, it is contemplated that vertebral plate 100 may include any suitable profile capable of securing adjacent vertebra thereto, such as square, oval, circular or the like.

Figure 2:
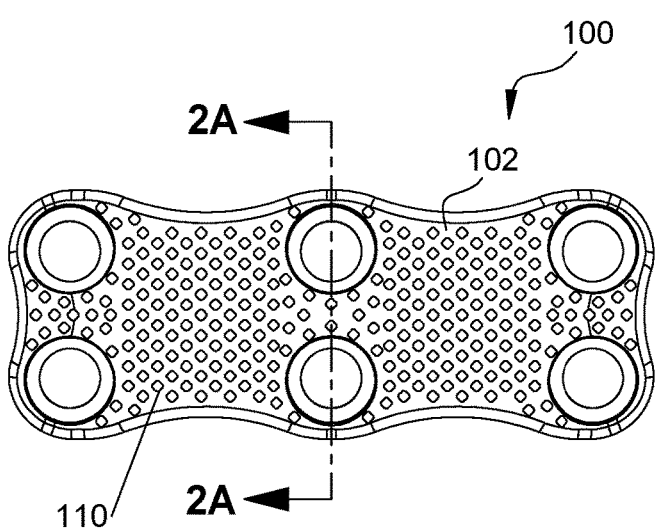
FIG. 2 is a top view of the vertebral plate of FIG. 1.
Figure 2A:
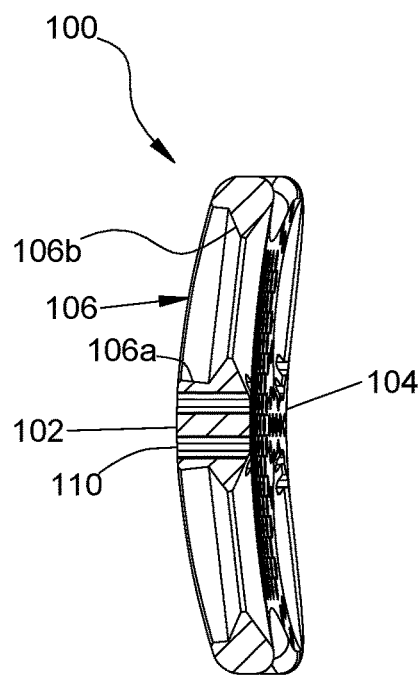
FIG. 2A is a cross-sectional view of the vertebral plate of FIG. 1, taken along line 2A-2A.
Figure 3:
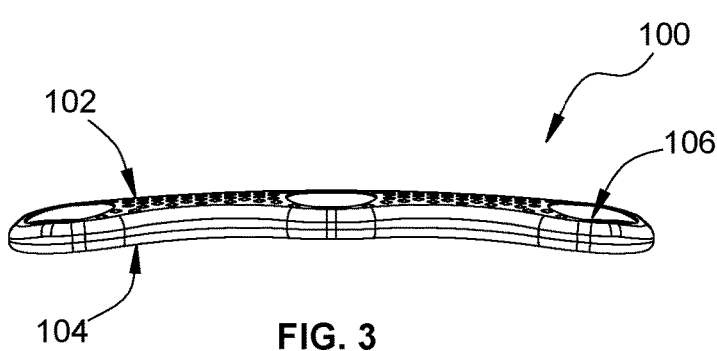
FIG. 3 is a side view of the vertebral plate of FIG. 1.

As best illustrated in FIGS. 2 and 2A, vertebral plate 100 includes a plurality of bone screw openings 106 defined therethrough configured to receive a corresponding plurality of bone screws or bone fixation elements 200 (FIG. 4A), as will be described in further detail hereinbelow. Each bone screw opening 106 is similar in construction, and therefore, only one will be described in detail hereinbelow. Bone screw opening 106 includes an annular sidewall 106a extending downwards from the top surface 102 of vertebral plate 100. A lip 106b is disposed in bone screw opening 106 and extends inwards from annular sidewall 106a, forming a generally frusto-conical configuration on an upper and lower side thereof. As can be appreciated, lip 106b may include any suitable profile, such as convex, concave, or the like. The lip 106b is disposed within bone screw opening 106 medially between top and bottom surfaces 102, 104 and is configured to engage a bone screw 200 (FIGS. 4A and 4B) such that rotating bone screw 200 causes the threads of an independent locking head 212 of bone screw 200 to engage lip 106b. In one non-limiting embodiment, lip 106b is located in proximity to the bottom surface 104 of vertebral plate 100.

Figure 6:
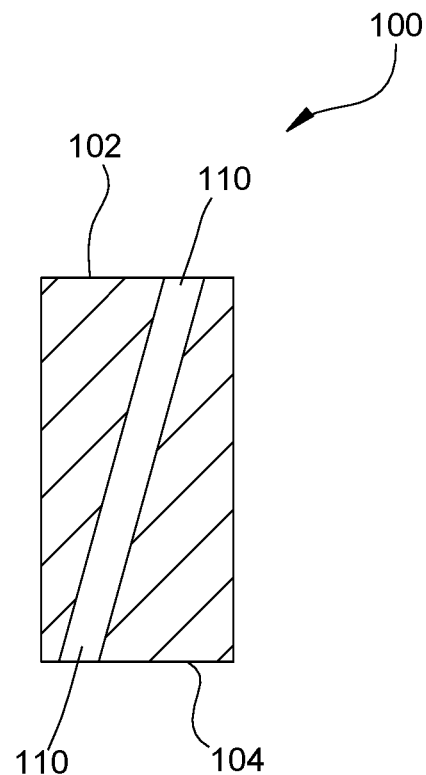
FIG. 6 is a cross-sectional view of the vertebral plate of FIG. 1 illustrating an orifice defined through an upper surface being offset from an orifice defined through a bottom surface.
Figure 7:
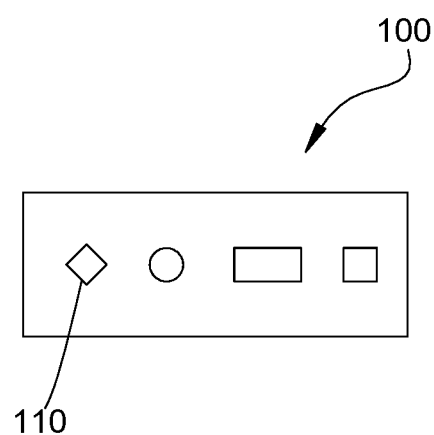
FIG. 7 illustrates various cross-sectional configurations of an orifice defined through the vertebral plate of FIG. 1.

Vertebral plate 100 is constructed of a biocompatible material, such as commercially pure titanium or titanium alloy and includes a porosity capable of promoting bone ingrowth with vertebral plate 100. In this manner, top and bottom surfaces 102, 104 have a surface roughness that can promote bone ingrowth. The surface roughness may be in a range of about 0.10-50 μm, and preferably in a range of about 3-4 μm. As can be appreciated, top and bottom surfaces 102, 104 may include the same or different surface roughness's (i.e., the surface roughness of top surface 102 may be different than the surface roughness of bottom surface 104), or top and bottom surfaces 102, 104 may not include a surface roughness; rather, top and bottom surfaces 102, 104 may be smooth. In embodiments, top and bottom surfaces 102, 104 may include any combination of surface roughness or smooth surface. Additionally, vertebral plate 100 includes a plurality of orifices 110 defined therethrough configured to promote bone ingrowth. Although generally illustrated as including a circular cross-section, orifices 110 may include any suitable cross-section capable of promoting bone ingrowth, such as oval, square, hexagonal, diamond, rectangular, or the like (FIG. 6). The circular cross-section of orifices 110 mimic bone growth along Haversian canals and lamellar structures of bone. In this manner, orifices 110 may pass entirely through top surface 102 and bottom surface 104 of vertebral body 100. Alternatively, orifices 110 may be offset in relation to one another (FIG. 7). In this manner, an orifice 110 defined through bottom surface 104 will be offset from a corresponding orifice 110 defined through top surface 102. In embodiments, orifices 110 may be defined through top and bottom surfaces 102, 104 normal thereto, at angles relative thereto. In one non-limiting embodiment, orifices 110 are defined through top and bottom surfaces at angles incident relative to each other, thereby forming a chevron configuration. As can be appreciated, each of the orifices 110 formed through top and bottom surfaces 102, 104 forms a respective channel therebetween, thereby interconnecting an orifice formed through top surface 102 and an orifice formed through bottom surface 104. It is contemplated that the density of orifices 110 may be different on top surface 102 than on bottom surface 104, or may increase or decrease in density at various locations on each of top and bottom surfaces 102, 104. Orifices 110 include a diameter in a range of about 50-1000 µm, although a diameter between 300-700 µm is preferable. As can be appreciated, for shapes other than circular, orifices 110 include a cross-sectional area in a range of about 0.0019 $\mu m^2$-0.785 $\mu m^2$, although a cross-sectional area between 0.0707 $\mu m^2$-0.385 $\mu m^2$ is preferable. As can be appreciated, the plurality of orifices 110 may include orifices 110 having varying sizes and shapes relative to each other. In embodiments, the orifices 110 defined through top surface 102 may include a different cross-section that those orifices 110 defined through bottom surface 104 (i.e., circular on top surface 102 while square on bottom surface 104, or vice versa). The plurality of orifices 110 reduce the density and stiffness of vertebral plate 100 to enable the application of bone putty or the like (e.g., bone morphogenetic proteins (BMP), etc.) to vertebral plate 100 to promote bone ingrowth within vertebral plate 100. Bone ingrowth strengthens vertebral plate 100 and reduces the load applied to bone screws 200. In this manner, the probability that vertebral plate 100 would fracture would be reduced, and the likelihood that micromotion would occur would likewise be reduced.

As can be appreciated, manufacturing vertebral plate 100 using standard machining methods (e.g., lathe, mill, EDM, etc.) would be difficult. In view of this, it is contemplated that vertebral plate 100 may be manufactured by means of additive manufacturing methods (e.g., SDM, SLPP, DMLS (i.e., EOS), SLS, SLM, SHS, EBM, VAT photopolymerisation, material jetting, binder jetting, or the like). In one non-limiting embodiment, vertebral plate 100 may be manufactured using Selective Laser Powder Processing (SLPP). SLPP utilizes powdered metal and a laser which sinters or cures the metal in a selective fashion according to the design intent in thin layers. In embodiments, the layers may have a thickness of about 250 µm. Vertebral plate 100 is built layer by layer to allow for more design options and features which would be difficult to be machined using conventional methods. Specifically, a first layer of powder is applied to a specialized build plate, at which point the laser cures portions of the powder according to the design intent. At this point, a second layer is applied to the build plate and the laser is again used to cure selective portions of this second layer. This process is repeated until vertebral plate 100 is fully formed. Once vertebral plate 100 is fully formed, uncured powder is removed using compressed air or other similar means. Next, post machining is performed on vertebral plate 100 to remove any burrs or similar imperfections embedded within vertebral plate 100 during the additive manufacturing process. In embodiments, the burrs are removed by means of buffer wheels, clipper, files, or the like. One de-burred, vertebral plate 100 is heat treated, and thereafter, media blasted using aluminum oxide. Thereafter, vertebral plate 100 is immersed in a hydrofluoric bath to strip the aluminum oxide therefrom. Finally vertebral plate 100 is inspected by quality control personnel (or using automated means), cleaned via ultrasonic cleaning, dried, and packaged. Additionally, using SLPP, it is contemplated that vertebral plate 100 may be customized for a designated patient. For a detailed description of exemplary manufacturing methods, reference can be made to U.S. Pat. No. 8,590,157, issued on Nov. 26, 2013 to Kruth et al., the entire contents of which are hereby incorporated by reference herein.

Vertebral plate 100 may be constructed from titanium, titanium alloy, cobalt-chrome, ceramic, polyetheretherketone (PEEK), or any other suitable biocompatible material. In embodiments, vertebral plate 100 may be manufactured using a three-dimensional printer utilizing a biocompatible polymer.

Figure 4A:
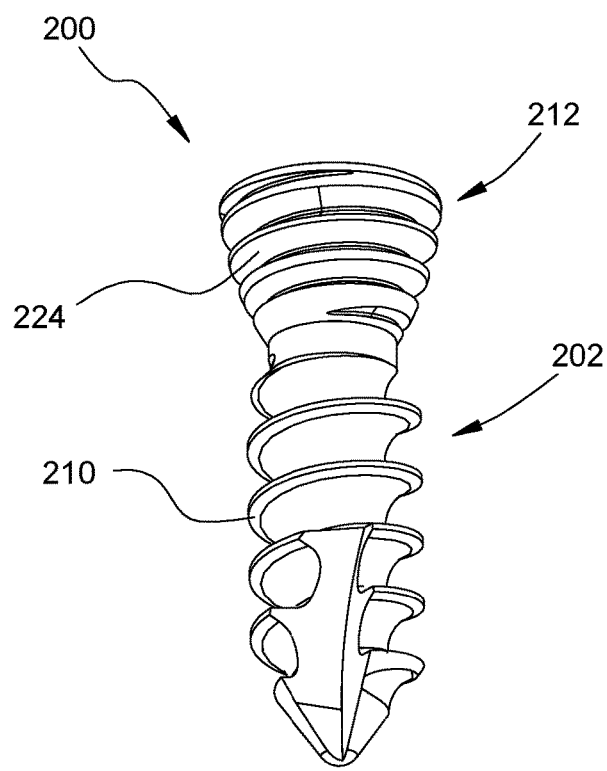
FIG. 4A is a bottom, perspective view, of a semi-constrained bone screw capable of use with the vertebral plate of FIG. 1.
Figure 4B:
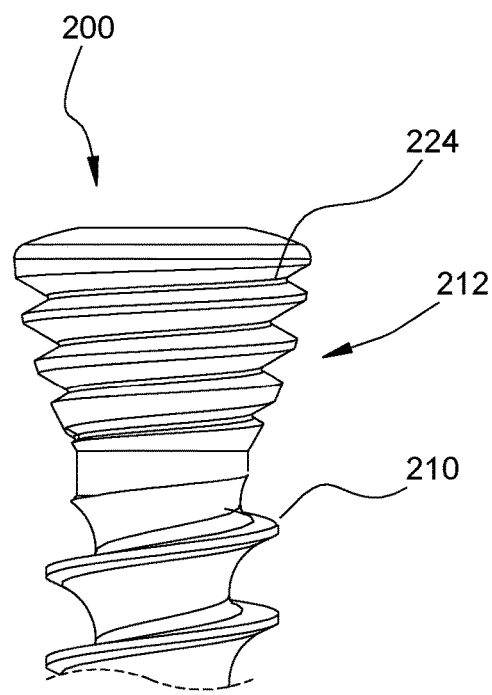
FIG. 4B is a side view of the semi-constrained bone screw of FIG. 4A.
Figure 4B:
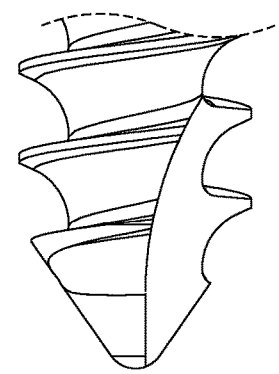

With reference to FIGS. 4A-4B, a bone screw provided in accordance with the present disclosure is provided and generally identified by reference numeral 200. Bone screw 200 includes an elongated shank 202, which is mechanically coupled to a removable tapered locking screw head 212. Shank 202 includes a uniform outer diameter and a first continuous helical thread 210 formed thereon for threaded insertion into bone. A second continuous helical thread 224 is formed on the independent head portion 212 for engaging lips 106b of vertebral plate 100. The pitch of the first thread 210 is greater than the pitch of the second thread 224. Each of the first and second threads 210, 224 includes a substantially uniform pitch. Preferably, bone screws 200 are constructed of a material which is harder than the material of lips 106b of vertebral plate 100. In embodiments, bone screws 200 may be formed of titanium alloy (e.g., Ti-6Al-4V) and the lips 106b of vertebral plate being formed from a softer material, such as commercially pure titanium. As can be appreciated, bone screws 200 may be monolithically formed such that head portion 212 of bone screws 200 is rigidly constrained in relation to shank 202.

Alternatively, bone screw 200 may be of a semi-constrained variety wherein the head portion is pivotable with respect to a longitudinal axis of the shank, thereby allowing the head portion to pivot while the shank remains stationary. For a detailed description of exemplary semi-constrained bone screws, reference may be made to U.S. Pat. No. 8,574,272, issued Nov. 5, 2013 to Wallenstein et al., and U.S. Pat. No. 9,095,390, issued Aug. 4, 2015 to Wallenstein et al., the entire contents of each of which are hereby incorporated by reference herein.

Figure 5A:
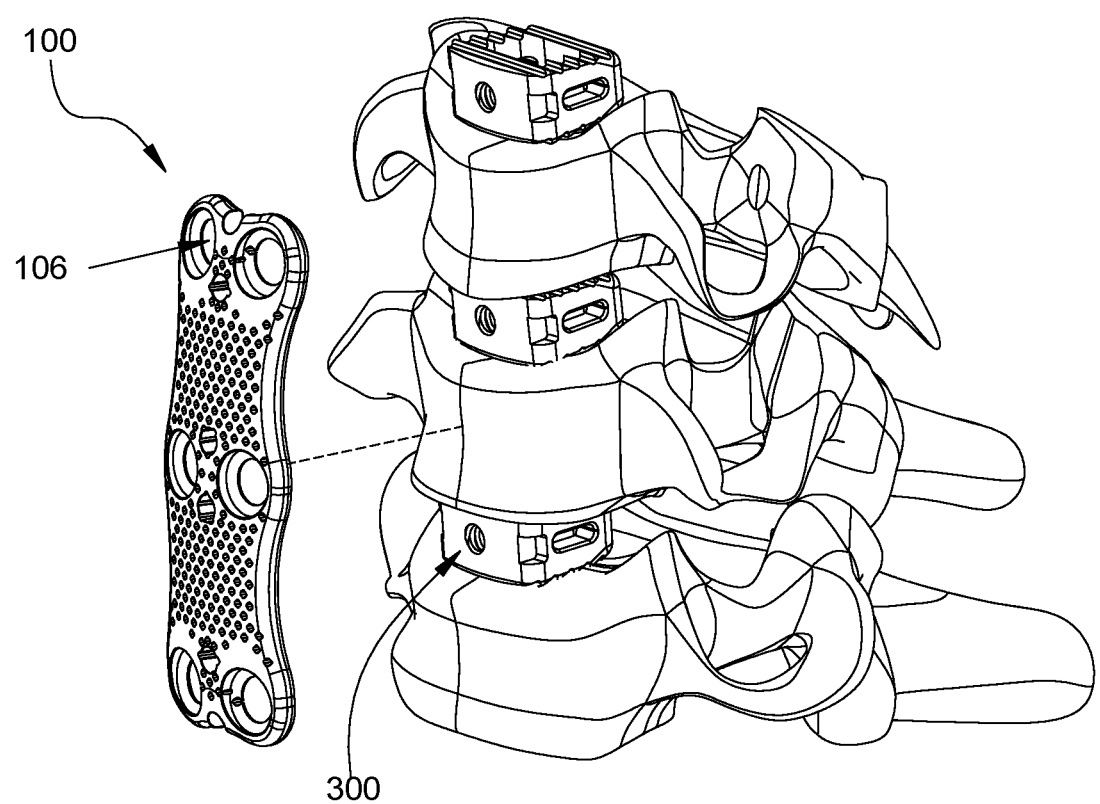
FIG. 5A is a perspective view of the vertebral plate of FIG. 1 shown as aligned with a spinal column of a patient having a vertebral spacer interposed between adjacent vertebral bodies.

In embodiments, it is contemplated that vertebral plate 100 and bone screws 200 may be provided in the form of a system or kit. As can be appreciated, the system or kit may include any suitable interbody spacer 300 (FIG. 5A). Interbody spacer 300 includes a body portion extending between distal and proximal end surfaces, respectively, to define top and bottom vertebral engaging surfaces and opposed side surfaces. The top and bottom surfaces each include a plurality of ridges disposed thereon to aid in securing interbody spacer 300 to each respective adjacent vertebral body and stability against fore and aft, oblique or side to side movement of interbody spacer 300 within the intervertebral space. For a detailed description of exemplary interbody spacers, reference can be made to U.S. Pat. No. 8,137,405, issued Mar. 20, 2012 to Kostuik et al., the entire contents of which are hereby incorporated by reference herein.

Figure 5B:
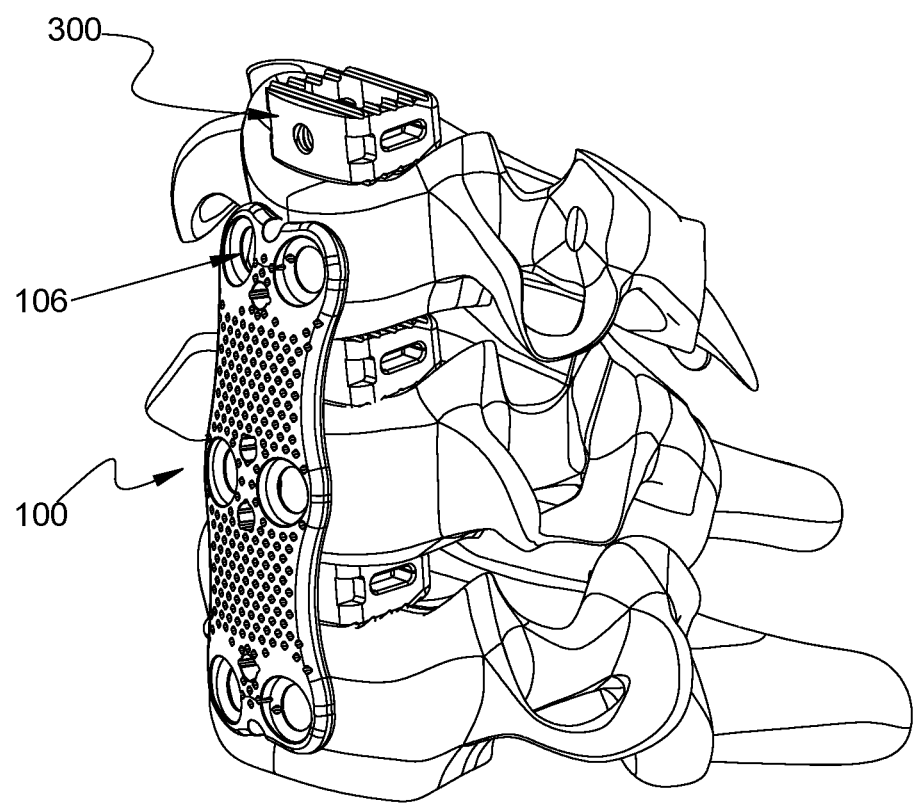
FIG. 5B is perspective view of the vertebral plate of FIG. 5A shown as being fastened to a plurality of vertebral bodies

With reference to FIGS. 1-5B, in use, vertebral plate 100 is inserted within an incision and aligned with adjacent vertebra (FIGS. 5A and 5B). At this point, bone screws 200 are advanced within each of the plurality of bone screw openings 106 of vertebral plate 100. Each bone screw 200 is driven into the vertebral body using a suitable tool or driver (not shown). As each bone screw 200 is further advanced, threads 224 of head portion 212 engage the lip 106b disposed within each bone screw opening 106. Continued advancement of the plurality of bone screws 200 deforms the lip 106b of vertebral plate 100 and secures the bone screw 200 in the corresponding bone screw opening 106 such that each bone screw 200 is inhibited from backing out of the respective bone screw opening 106. Further, head portion 212 of bone screw 200 is dimensioned to engage lip 106b to prevent further advancement of bone screw 200 through vertebral plate 100. This type of screw locking arrangement is disclosed and shown in U.S. Pat. No. 6,322,562, issued Nov. 27, 2001 to Wolter, the entire contents of which are hereby incorporated by reference herein.

As threads 220 of the screw head 212 engage the corresponding lip 106b, screw shank 202 varies in angular orientations with respect to the axis of the bone screw opening 106. As screw shank 202 is driven into bone and the screw head 212 locked to vertebral plate 100, the screw shank 202 remains free to articulate relative to the screw head 212 and, hence, vertebral plate 100. At this point, bone growth putty or other suitable compositions (e.g., BMP, etc.) may be applied to vertebral plate 100 to promote bone ingrowth. In embodiments, an interbody spacer 300 is first advanced within a prepared intervertebral space. In this manner, the vertebral plate 100 helps prevent the interbody spacer 300 from being forced out of the intervertebral space (FIGS. 5A and 5B).

For a detailed description of exemplary methods of using a vertebral plate with semi-constrained bone screws, reference may be made to U.S. Pat. No. 8,574,272, incorporated by reference hereinabove.

This process may be repeated as many times as the procedure requires, whether it be for the same vertebral plate 100 or for a plurality of vertebral plates 100 as required by the procedure being performed.

It is envisioned that the manufacturing processes and orifice designs detailed above may be utilized to form various other medical devices known in the art. In this manner, the additive manufacturing process detailed above may be employed to form corpectomy devices, fixed spinal implants, expandable spinal implants, bone screws, cervical implants, and the like. Similarly, the orifice designs detailed above may be formed in any of the before mentioned medical devices that would benefit from an increased ability to fuse with bone. Examples of such devices may be found in the following commonly owned references: U.S. Pat. No. 8,585,761 to Theofilos, U.S. Pat. No. 8,673,011 to Theofilos et al., U.S. application Ser. No. 14/936,911 to Sutterlin et al., U.S. Pat. No. 8,801,791 to Soo et al., U.S. Pat. No. 8,439,977 to Kostuik et al., U.S. Patent Application Publication No. 2010/0100131 to Wallenstein, U.S. Patent Application Publication No. 2012/0179261 to Soo, U.S. Pat. No. 8,449,585 to Wallenstein et al., U.S. Pat. No. 8,814,919 to Barrus et al., U.S. Pat. No. 5,733,286 to Errico et al., U.S. Patent Application Publication No. 2013/0046345 to Jones et al., U.S. Pat. No. 8,961,517 to McClintock et al., U.S. Patent Application Publication No. 2015/0025573 to Abitbol et al., and U.S. Patent Application Publication No. 2015/0142062 to Donald et al.

It will be understood that various modifications may be made to the embodiments of the presently disclosed vertebral plate. Therefore, the above description should not be construed as limiting, but merely as exemplifications of embodiments. Those skilled in the art will envision other modifications within the scope and spirit of the present disclosure.

The invention claimed is:

1. A vertebral plate, comprising:
a top surface and a bottom surface;
a plurality of channels each extending between the top and bottom surfaces, each of the channels bounded by a first orifice defined in the top surface and a second orifice defined in the bottom surface, each of the channels comprising a longitudinal axis, wherein a cross-sectional dimension of each channel is constant along its longitudinal axis,
the first orifice having a first cross-sectional shape and defining a first axis through a centerpoint thereof that is normal to the top surface, and the second orifice having a second cross-sectional shape different from the first cross-sectional shape and defining a second axis through a centerpoint thereof that is normal to the bottom surface; and
a plurality of bone screw openings defined through the top and bottom surfaces,
wherein a largest cross-sectional dimension of each channel is smaller than a smallest cross-sectional dimension of each of the bone screw openings, and
wherein the channels outnumber the bone screw openings by more than double.

2. The vertebral plate of claim 1, further including a lip defined within each bone screw opening of the plurality of bone screw openings, each lip configured to engage a corresponding bone screw to retain the corresponding bone screw therein.

3. The vertebral plate of claim 1, wherein the top and bottom surfaces include concave curvatures.

4. The vertebral plate of claim 3, wherein the concave curvatures of the top and bottom surfaces extend in a cephalad/caudal direction.

5. The vertebral plate of claim 3, wherein the concave curvatures of the top and bottom surfaces extend in a medial/lateral direction.

6. The vertebral plate of claim 3, wherein the concave curvatures of the top and bottom surfaces extend in both a cephalad/caudal direction and a medial/lateral direction.

7. The vertebral plate of claim 1, wherein the vertebral plate is formed using an additive manufacturing process.

8. The vertebral plate of claim 7, wherein the additive manufacturing process comprises Selective Laser Powder Processing.

9. The vertebral plate of claim 1, wherein each bone screw opening of the plurality of bone screw openings is separate and distinct from the plurality of channels.

10. A vertebral plate system, comprising:
a vertebral plate including:
   a top surface and a bottom surface;
   a plurality of channels extending between the top and bottom surfaces, each of the channels bounded by a first orifice defined in the top surface and a second orifice defined in the bottom surface,
each of the channels comprising a longitudinal axis, wherein a cross-sectional dimension of each channel is constant along its longitudinal axis,
   the first orifice having a non-circular cross-sectional shape and defining a first axis through a centerpoint thereof, and the second orifice having a non-circular cross-sectional shape defining a second axis through a centerpoint thereof, the first and second axes being coaxial with the longitudinal axis of the respective channel, the longitudinal axis of each channel being oriented at an oblique angle relative to the top and bottom surfaces;
   a plurality of bone screw openings defined through the top and bottom surfaces; and
   a plurality of bone screws each configured to be advanced within one of the plurality of bone screw openings and driven into bone,
      wherein there are at least twice as many channels as bone screw openings.

11. The system of claim 10, wherein each bone screw of the plurality of bone screws is a semi-constrained bone screw.

12. The system of claim 11, wherein the semi-constrained bone screws each include a shank having a first helical thread disposed thereon and a second helical thread disposed on a head portion thereof.

13. The system of claim 12, wherein a pitch of the first helical thread is different than a pitch of the second helical thread of each semi-constrained bone screw, such that the first helical thread is configured to thread into vertebral bone whereas the second helical thread is configured to engage a lip disposed within one of the plurality of bone screw openings, thereby retaining each semi-constrained bone screw within the vertebral plate.

14. The vertebral plate system of claim 10, wherein each bone screw opening of the plurality of bone screw openings is separate and distinct from the plurality of channels.

15. A method of performing spinal surgery, comprising:
   inserting a vertebral plate into an incision of a patient, the vertebral plate including:
      a top surface and a bottom surface;
      a plurality of channels each extending between the top and bottom surfaces and along a longitudinal axis thereof, the channels each being bounded by a first orifice defined in the top surface and a second orifice defined in the bottom surface, the first and second orifices each having different cross-sectional shapes, wherein a cross-sectional dimension of each channel is constant along its longitudinal axis; and
      a plurality of bone screw openings defined through the top and bottom surfaces,
         wherein a largest cross-sectional dimension of each of the plurality of channels is smaller than a smallest cross-sectional dimension of each of the bone screw openings, and wherein there are more than twice as many channels as bone screw openings;
      advancing a bone screw of a plurality of bone screws within each bone screw opening of the plurality of bone screw openings; and
      driving each bone screw of the plurality of bone screws into a bone.

16. The method of claim 15, further including applying a material to the vertebral plate to promote bone ingrowth within the first and second orifices.

17. The method of claim 15, wherein driving each bone screw of the plurality of bone screws into a bone includes driving a plurality of semi-constrained bone screws into a bone.

18. The method of claim 17, wherein driving the plurality of semi-constrained bone screws into a bone includes threading a first helical thread disposed on a shank of each of the semi-constrained bone screws into the bone and engaging a second helical thread disposed on a head of each of the semi-constrained bone screws with a lip disposed within a corresponding bone screw opening of the plurality of bone screw openings, thereby retaining the plurality of semi-constrained bone screws within the vertebral plate.

19. The method of claim 15, wherein the method further includes advancing an interbody spacer within a prepared intervertebral space before advancing each bone screw of the plurality of bone screws within the corresponding bone screw opening of the plurality of bone screw openings.

20. The method of claim 16, wherein applying a material to the vertebral plate includes applying a bone growth putty to the vertebral plate to promote bone ingrowth within the first and second orifices.

* * * * *